United States Patent [19]

Staffieri

[11] 4,268,923
[45] May 26, 1981

[54] THIGH PROSTHESIS

[76] Inventor: Lamberto Staffieri, Via Matteotti 28, Torbole Sul Garda, Italy

[21] Appl. No.: 112,763

[22] Filed: Jan. 17, 1980

[51] Int. Cl.³ .......................... A61F 1/04; A61F 1/08
[52] U.S. Cl. .............................................. 3/22; 3/29
[58] Field of Search ...................................... 3/22–29, 3/2

[56] References Cited

U.S. PATENT DOCUMENTS

| | | | |
|---|---|---|---|
| 2,542,567 | 2/1951 | Peters | 3/29 X |
| 3,806,958 | 4/1974 | Gusev | 3/22 |
| 3,820,169 | 6/1974 | Long et al. | 3/22 |
| 3,823,424 | 7/1974 | May | 3/22 |

FOREIGN PATENT DOCUMENTS

| | | | |
|---|---|---|---|
| 599440 | 10/1925 | France | 3/22 |
| 175193 | 2/1922 | United Kingdom | 3/27 |

Primary Examiner—Ronald L. Frinks
Attorney, Agent, or Firm—Guido Modiano; Albert Josif

[57] ABSTRACT

A thigh prosthesis or artificial leg comprising an upper socket portion designed to be secured, in use, to an amputee's stump, a lower leg portion, an articulation frame joining the socket portion to the leg portion, and resilient means for limiting and cushioning the articulation motion of the said articulation frame.

The thigh prosthesis or artificial leg in accordance with the present invention lengthens during active deambulation phases and shortens during passive deambulation phases, thereby making it possible for the user to keep his center of gravity substantially at the same level during deambulation and to take advantage to a maximum extent of his instinctive sense of balance.

6 Claims, 4 Drawing Figures

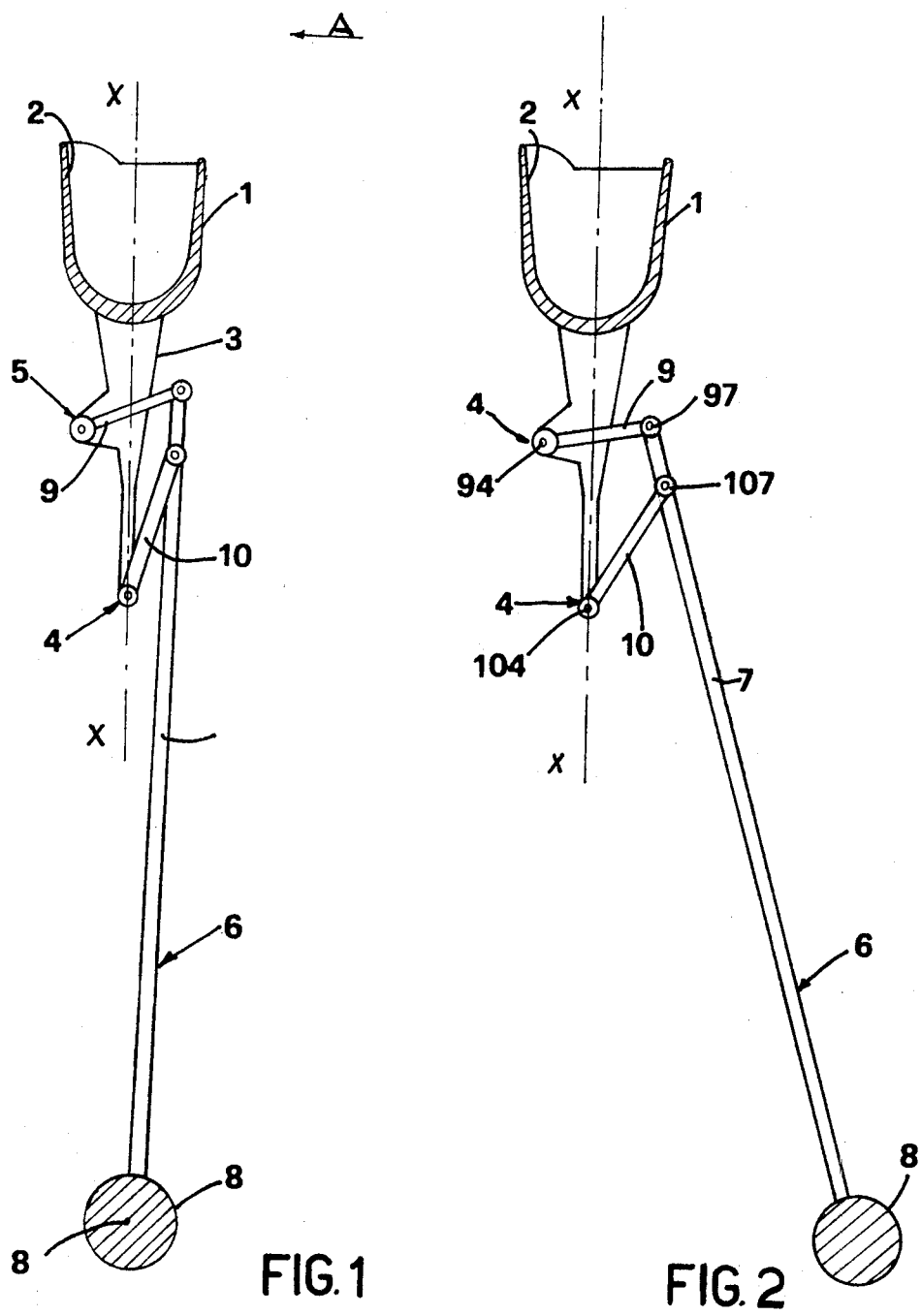

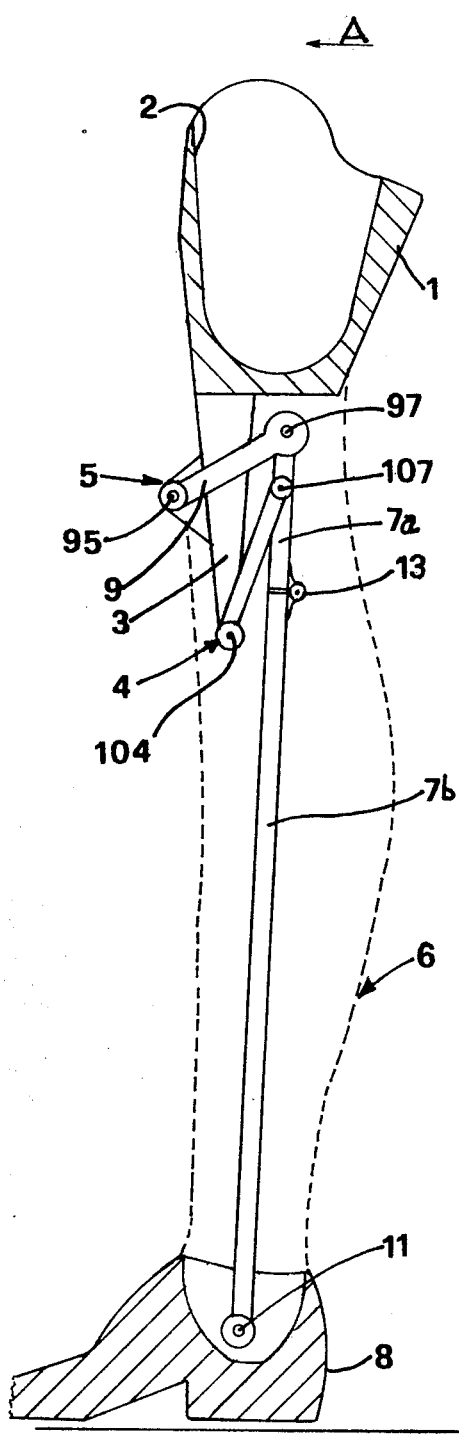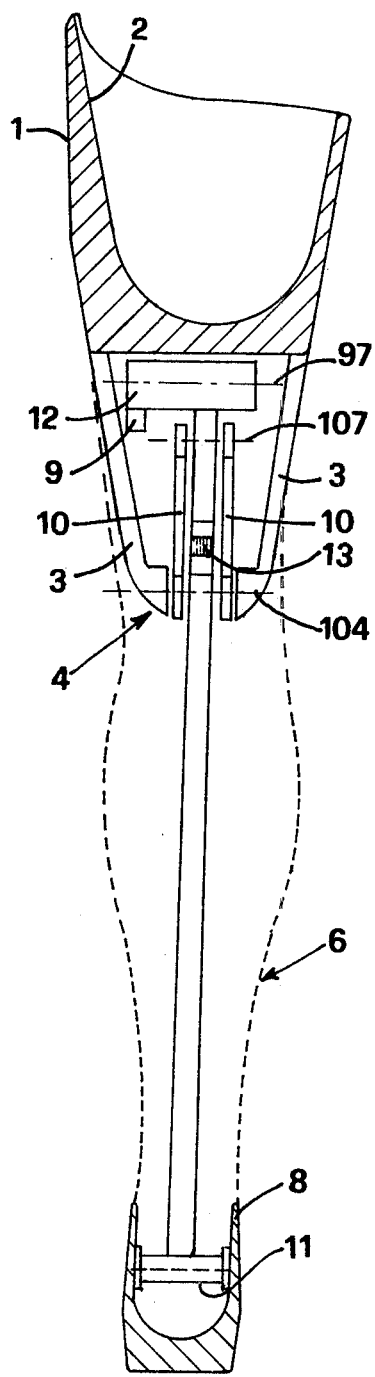

THIGH PROSTHESIS

BACKGROUND OF THE INVENTION

The present invention relates to a thigh prosthesis or artificial leg designed to permit instinctive movements that amputees to whom a thigh has been amputated should effect to be able to keep in balance on the carrying axis of the artificial leg and to walk.

An amputee to whom a thigh has been amputated is generally given an artificial leg or thigh prosthesis designed to be of the same length as his non-amputated leg. Such a prosthesis is often unsatisfactory as it is only suitable to ensure static balance.

For dynamic balance a thigh prosthesis sensitive to motion variatious is required.

Moreover, many thigh prosthesis of the prior art are quite cumbersome to use and difficult and expensive to manufacture. Some conventional artificial legs are also provided with braking devices to prevent the user from falling. However, braking devices are generally useless as they exert positive action only when the user has already lost his balance.

Furthermore, prior art artificial legs are designed to shorten during advance movement of the user's non-amputated leg (active deambulation phase), which results in the amputee's center of gravity being considerably lowered. Thus, in the deambulation passive phase (i.e. when the artificial leg is lifted by the user to allow it to lengthen) the user must effect a considerable additional effort to raise his own center of gravity.

SUMMARY OF THE INVENTION

An object of this invention is to provide a thigh prosthesis or artificial leg capable of providing static and dynamic balance while giving the amputee the possibility of taking advantage of his instinctive sense of balance.

Another object of the invention is to provide an artificial leg designed to prevent the user's center of gravity from lowering to a substantial extent during deambulation.

Another object of the invention is to provide a thigh prosthesis adapted to simulate a natural gait.

Another object of the invention is the provision of an artificial leg simple to produce and use and which may be manufactured at low cost.

These and other objects are attained by a thigh prosthesis or artificial leg comprising an upper socket portion designed to be secured, in use, to an amputee's stump, a lower leg portion, an articulation frame joining the socket portion to the leg portion, and resilient means for limiting and cushioning the articulation motion of the said articulation frame;

the said socket portion having a downwardly extending projection carrying a lower pivot mounting and an upper pivot mounting which is arranged in a forward position, in the forward deambulation direction, with respect to the said lower pivot mounting and is in vertical misalignment therewith;

the said leg portion comprising a rod or bar carrying a weight or foot at its lower end and being linked to the said articulation frame at, or close to, its upper end; and the said articulation frame includes at least one upper link transversely extending with respect to the said downwardly extending projection and being secured at one end thereof to the said upper pivot mounting and at the other end thereof to the said upper end of said rod or bar, and at least one lower link having one end pivotally secured to the said lower pivot mounting and its other end pivotally secured to the said rod or bar in an intermediate position thereof close to its upper end.

BRIEF DESCRIPTION OF THE DRAWINGS

Other and further object and advantageous features of the present invention will become more apparent from the following detailed description of the accompanying drawings, in which:

FIGS. 1 and 2 are diagrammatic views showing the principle of operation of a thigh prosthesis in accordance with the invention;

FIG. 3 is a sectional view along a vertical plane of an embodiment of the prosthesis of FIGS. 1 and 2; and FIG. 4 is a sectional view of the prosthesis of FIG. 1 taken along a vertical plane at right angles with respect to that of FIG. 1.

DETAILED DESCRIPTION OF A PREFERRED EMBODIMENT

Referring to the drawings in detail, reference numeral 1 indicates an upper socket portion of a thigh prosthesis or artificial leg in accordance with the invention. The socket portion 1 delimits inside thereof a recess 2 designed to receive the stump of an amputated leg. As shown in FIGS. 1 and 2 the socket portion 1 has a downwardly projecting extension 3 which carries a lower pivot mounting 4 and an upper pivot mounting 5. The pivot mounting 5 is disposed in a forward position, in the forward deambulation direction A, with respect to the pivot mounting 4 and is not, in use, in vertical alignment therewith. The pivot mounting 4 is arranged, in use, on the vertical axis x—x passing through the user's center of gravity.

The thigh prosthesis also comprises a lower leg portion 6 which includes a bar or rod 7 and a weight 8 shaped as a foot in FIGS. 3 and 4.

The socket portion 1 and the leg portion 6 are linked to one another by means of an articulation frame comprising connecting links 9 and 10. More particularly, the link 9 has one end articulated to the upper end of the rod 7 through a pivot axis 97, and its other end attached to the pivot mounting 5 by way of a pivot axis 94.

It will be noted that the link 9 extend transversally with respect to vertical axis x—x.

The link 10 has one end attached to the pivot mounting 4 through a pivot axis 104 and its other end articulated through a pivot axis 107 to the rod 7, the pivot axis 107 being arranged at a level higher than that of the pivot axis 104 in a position close to the pivot axis 97.

It will be seen that the extension 3, the links 9 and 10 and the bar 7 are the components of a specific parallelogram frame arranged to permit the rod 7, when the socket portion 1 is displaced forward in the direction of the arrow A, to be moved from a standing position (shown in FIG. 1) to an extended position (shown in FIG. 2). While in its standing position, the rod 7 is arranged slightly inclined with respect to the axis x—x and crosses it at a point 8a close to the ground level. In the extended position the weight 8 is spaced apart from the axis x—x by being left behind by the socket portion when moved forward by the user.

As soon as the user effects a deambulation passive phase (as defined above) the weight 8 will move mostly by gravity towards the axis x—x to the position shown in FIG. 1. The extent to which the weight or foot 8 can move to and from the axis x—x is determined by resilient abutment or similar limit means, not shown. Such limit means for instance may be attached to the socket portion 1 or to its extension 3 and act on one of the links 9 or 10. Moreover, limit means may be provided inside the foot 8 (FIGS. 3 and 4) and arranged to act on the rod 7 which is pivotally connected to the foot 8 through a pivot pin 11.

Advantageously, the pivot connection between the rod 7 and the link 9 is of a resilient type, e.g. including a spring housed in a sleeve 12 (FIG. 4) and having one end connected to the link 9 and its other end acting on the rod 7 to yieldingly resist relative movement of link 9 and rod 6 and to assist forward movement of the weight 8 from the position shown in FIG. 2 to that shown in FIG. 1. Further resilient means, such as pieces of rubber can be provided to support the pin 11 to better cushion the leg movements, as is well known in the art.

Advantageously the rod 7 comprises two sections 7a and 7b articulated to one another by means of a hinge 13 (FIG. 3) to allow the user to manually bend the artificial leg, e.g. when sitting on a chair.

From the foregoing description it is readily apparent that the present invention provides a thigh prosthesis or artificial leg which lengthens during active deambulation phases and shortens during passive deambulation phases, thereby making it possible for the user to keep his center of gravity substantially at the same level during deambulation and to take advantage to a maximum extent of his instinctive sense of balance.

While the present invention has been described in particular relation to the accompanying drawings, it is understood that other modifications and variations apart from those shown and described herein may be made within the spirit and scope of this invention.

I claim:

1. A thigh prosthesis or artificial leg comprising an upper socket portion designed to be secured, in use, to an amputee's stump, a lower leg portion, an articulation frame joining the socket portion to the leg portion, and resilient means for limiting and cushioning the articulation motion of the said articulation frame;

the said socket portion having a downwardly extending projection carrying a lower pivot mounting and an upper pivot mounting which is arranged in a forward position, in the forward deambulation direction, with respect to the said lower pivot mounting and is in vertical misalignment therewith;

the said leg portion comprising a rod or bar carrying a weight or foot at its lower end and being linked to the said articulation frame at, or close to, its upper end; and the said articulation frame includes at least one upper link transversely extending with respect to the said downwardly extending projection and being secured at one end thereof to the said upper pivot mounting and at the other end thereof to the said upper end of said rod or bar, and at least one lower link having one end pivotally secured to the said lower pivot mounting and its other end pivotally secured to the said rod or bar in an intermediate position thereof close to its upper end.

2. A thigh prosthesis as set forth in claim 1, wherein the said lower pivot mounting is arranged, in use, substantially on the vertical axis passing through the user's center of gravity, and the said lower leg portion is located backwards, in the deambulation direction, with respect to the said lower pivot mounting and is reciprocally movable, during deambulation, from a standing position in which it crosses the said vertical axis at a point close to the ground level to an extended position in which its weight or foot is spaced apart from the said vertical axis.

3. A thigh prosthesis as set forth in claim 2, wherein the said socket portion has a first and a second downwardly projecting extension, the said first extension being arranged substantially along the said vertical axis and carrying the said lower pivot mounting, and the said second extension carrying the said upper pivot mounting.

4. A thigh prosthesis as set forth in claim 1, wherein the said resilient means comprises a spring-loaded articulation.

5. A thigh prosthesis as set forth in claim 1, comprising one upper link and a pair of lower links.

6. A thigh prosthesis as set forth in claim 1, wherein the said rod or bar comprises two sections hinged to one another.

* * * * *